(12) United States Patent
Wagner et al.

(10) Patent No.: US 10,661,000 B2
(45) Date of Patent: May 26, 2020

(54) METHOD FOR CONVEYING A MEDIUM WITH A PUMP AND PUMP COMPRISING A ROTOR, A HOUSING AND A DRIVE

(71) Applicant: Xenios AG, Heilbronn (DE)

(72) Inventors: Ozan Wagner, Offenau (DE); Sven Filipon, Heilbronn (DE); Benjamin Brueckner, Heilbronn (DE)

(73) Assignee: Xenios AG, Heilbronn (DE)

(*) Notice: Subject to any disclaimer, the term of this patent is extended or adjusted under 35 U.S.C. 154(b) by 96 days.

(21) Appl. No.: 15/567,716

(22) PCT Filed: Mar. 18, 2016

(86) PCT No.: PCT/DE2016/000118
§ 371 (c)(1),
(2) Date: Nov. 28, 2017

(87) PCT Pub. No.: WO2016/169540
PCT Pub. Date: Oct. 27, 2016

(65) Prior Publication Data
US 2018/0117227 A1    May 3, 2018

(30) Foreign Application Priority Data

Apr. 20, 2015  (DE) .................. 10 2015 004 968

(51) Int. Cl.
*A61M 1/10*        (2006.01)
(52) U.S. Cl.
CPC .......... *A61M 1/1086* (2013.01); *A61M 1/101* (2013.01); *A61M 1/1005* (2014.02);
(Continued)

(58) Field of Classification Search
CPC .. A61M 1/101; A61M 1/1005; A61M 1/1013; A61M 1/1029; A61M 1/1031; A61M 1/1036; A61M 2205/3327
See application file for complete search history.

(56) References Cited

U.S. PATENT DOCUMENTS 3,689,204 A * 9/1972 Prisk ................... F04B 43/0054
                                                    417/394
5,437,634 A    8/1995 Amano
(Continued)

FOREIGN PATENT DOCUMENTS

CN      102076367 A    5/2011
EP      0 665 024 A1   8/1995
(Continued)

OTHER PUBLICATIONS

International Search Report of PCT/DE2016/000118, dated Sep. 26, 2016.
(Continued)

*Primary Examiner* — Paula J Stice
(74) *Attorney, Agent, or Firm* — Collard & Roe, P.C.

(57) ABSTRACT

A method for conveying blood or priming liquid as a medium using a blood pump, measures gas in the medium in a feed line to the pump, in or on the pump, and the pump power is increased only for a short time as a function of the measured gas. A blood pump, in particular a centrifugal pump or diagonal pump, includes a rotor, a housing and a drive, the pump including a gas detector which acts upon the drive when gas is detected.

18 Claims, 1 Drawing Sheet

(52) U.S. Cl.
CPC ......... *A61M 1/1013* (2014.02); *A61M 1/1029* (2014.02); *A61M 2205/3327* (2013.01)

(56) References Cited

U.S. PATENT DOCUMENTS

| | | | |
|---|---|---|---|
| 5,676,526 | A | 10/1997 | Kuwana et al. |
| 5,965,089 | A | 10/1999 | Jarvik et al. |
| 6,716,189 | B1 | 4/2004 | Jarvik et al. |
| 7,022,099 | B2 | 4/2006 | Litzie et al. |
| 7,264,606 | B2 | 9/2007 | Jarvik et al. |
| 2004/0184953 | A1* | 9/2004 | Litzie .............. A61M 1/3629 422/45 |
| 2006/0009728 | A1 | 1/2006 | Litzie et al. |
| 2006/0089586 | A1 | 4/2006 | Kaus et al. |
| 2011/0118998 | A1 | 5/2011 | Loose et al. |

FOREIGN PATENT DOCUMENTS

| | | |
|---|---|---|
| JP | H06-121831 A | 5/1994 |
| JP | H07-47121 A | 2/1995 |
| JP | 2001-523983 A | 11/2001 |
| JP | 2006-520650 A | 9/2006 |
| JP | 2008-517651 A | 5/2008 |
| JP | 2010-077948 A | 4/2010 |
| WO | 98/14225 A2 | 4/1998 |
| WO | 2004/082467 A2 | 9/2004 |
| WO | 2006/047147 A1 | 5/2006 |

OTHER PUBLICATIONS

Johann Friederich Gülich: Kreiselpumpen 3, Auflage, Heidelberg: Springer, 2010, 298, 680-681, 772-780, ISBN 978-3-642-05478-5, 13 pages (2010).

Japanese Search Report in Japanese Application 2017-555245, dated Dec. 26, 2019, with English translation.

Notice of Reasons for Refusal in the Japanese Application 2017-555245, dated Jan. 7, 2020, with English translation.

* cited by examiner

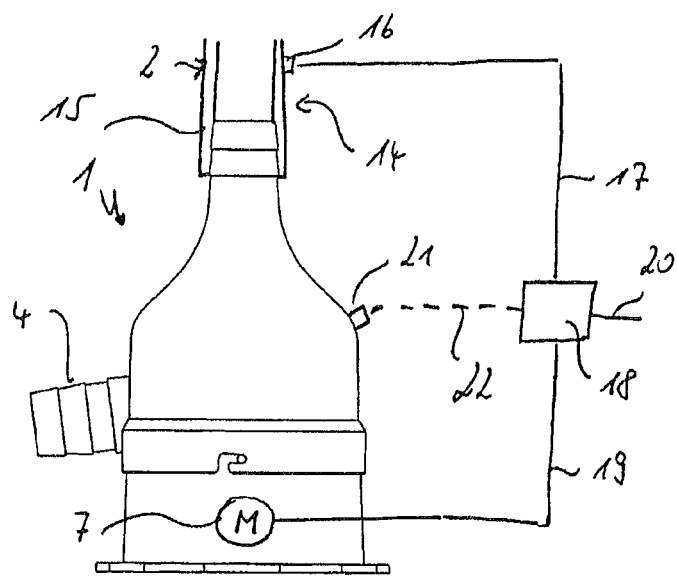
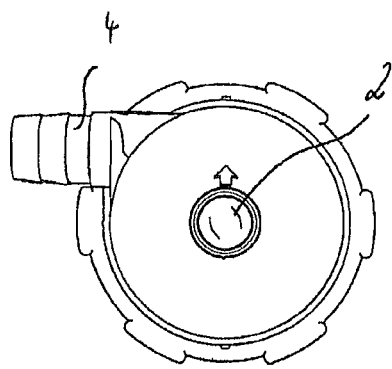
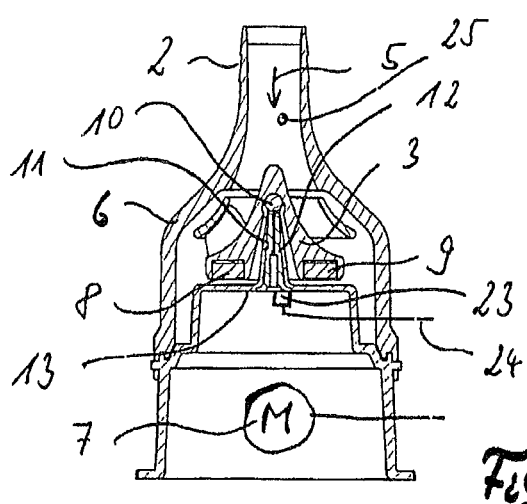

METHOD FOR CONVEYING A MEDIUM WITH A PUMP AND PUMP COMPRISING A ROTOR, A HOUSING AND A DRIVE

CROSS REFERENCE TO RELATED APPLICATIONS

This application is the National Stage of PCT/DE2016/000118 filed on Mar. 18, 2016, which claims priority under 35 U.S.C. § 119 of German Application No. 10 2015 004 968.2 filed on Apr. 20, 2015, the disclosure of which is incorporated by reference. The international application under PCT article 21(2) was not published in English.

The invention relates to a method of conveying blood or priming fluid as the medium, with a blood pump and a pump with a rotor, a housing and an actuator.

In the field of medical technology, pumps, such as in particular centrifugal pumps or diagonal pumps, are used to convey blood. In contrast to roller pumps these have the essential advantage that they protect the blood. A disadvantage of centrifugal pumps lies in the fact that they cannot convey onwards air that enters the centrifugal pump. The air usually becomes trapped in the rotor and impairs the performance of the centrifugal pump. Overheating may even occur on the rotor bearing which can result in damage to the blood pump and the blood.

For large rotary pumps it is described in Johann Friedrich Güllich Kreiselpumpen, 3rd edition, Heidelberg: Springer 2010. 298, 680-681, 772-780-ISBN 978-3-642-05478-5 that the pump can be regulated up to a particular flow rate and in the event of gas bubbles the conveying capacity is then inevitably increased. In the case of a blood pump, if there is gas in the pump such regulation would lead to an increase in the conveying capacity and the blood being damaged.

The object of the invention is to propose a method of conveying a medium with a blood pump, in particular a centrifugal pump or a diagonal pump, which results in such damage being ruled out. The aim of the invention is also to further develop a pump of the type in question in such a way that such negative effects are no longer to be feared.

In terms of the method this task is solved with the features described herein and in terms of the device with the features described herein.

It has been established that even a short-term increase in the output of the pump through increasing its speed is sufficient to hurls the air bubbles accumulating in the area of the rotor bearing outwards so that they are conveyed out of the pump with the flow of blood. It is therefore proposed that in the conveyed medium the gas is measured and the output of the pump only increased briefly as a function of the measured gas. This allows the gas that has entered, which could lead to a reduction in output or damage to the pump, to be detected early and by means of acceleration of the pump blades the accumulating gas bubbles to be ejected, or even an accumulation of gas to be prevented.

The method according to the invention can be used for every pump in which fluid is moved by a rotor and conveyed from an inlet to an outlet. Preferably this method is used in a centrifugal pump or a diagonal pump.

Particularly advantageous is a pulsatile mode in the pump or in the blood flow. The result of this is that during the brief moment of reduced volumetric flow the air has the opportunity of detaching itself from the rotor. The subsequent thrust brought about by the increased blood flow then conveys the air bubble out of the pump through the blood outlet. In this way the pump becomes free of air in a simple manner.

In order to be able to react to gas entry early, the gas can be measured in an inlet line to the pump. The measuring device can be set to a particular air bubble diameter harbouring the risk of air bubbles with this diameter accumulating in the blood pump. In addition, the measurement can cumulatively over a period of time add together the bubble volumes supplied to the blood pump in order to briefly increase the output of the pump as of a predetermined threshold so that the accumulated air is conveyed out of the pump.

Alternatively or additionally it is proposed that the gas in or on the pump, for example on the pump housing, is measured. This makes it easier to determine the gas quality actually accumulated in the pump so as to react through increasing the pump output when a critical quantity is exceeded.

Increasing the pump output results in special centrifugal forces which not only hurl the blood, but also the case accumulated gas in the blood pump, radially outwards, carrying it along with the flowing blood. Generally it is sufficient for the pump output only to be increased briefly. Therefore as a blood pump a pump is proposed with conveys around 0 to 8 l/min at a speed of a maximum of 10,000 l/min.

Experiments have shown that it is sufficient for the pump output to be increased for a period of less than 5 seconds and preferably up to 2 seconds. Every increase in output results in the time period of the output increase being greater than 0 seconds. In practice the time period of the output increase is above 0.1 seconds and around 0.1 to 2 seconds.

In addition to the duration of the increase in output, the gradient of the increase in pump output is relevant for removing the accumulated gas in the centrifugal pump in the shortest possible time through increasing the volumetric flow. It is therefore proposed that the pump output is increased by up to 100% within a period of 5 seconds and preferably of up to 2 seconds. In other words the pump output should preferably be increased to double the output within a period of less than 2 seconds in order to convey the blood out of the pump through the strong acceleration.

More particularly, in order to achieve such accelerations without damaging the conveyed medium through too high a power input, it is proposed that the pump output is reduced before the increase. A brief reduction before the increase allows a protecting increase in output for a short period. Every reduction in output results in the time period of the output reduction being greater than 0 seconds. In practice the time period of output reduction is above 0.1 seconds and around 0.1 to 2 seconds.

In accordance with the dynamics during the increase in output it is also advantageous if before the increase the output is rapidly reduced. It is therefore proposed that the before the increase the pump output is reduced by up to 100% within a period of less than 5 seconds and preferably of up to 2 seconds. Through this brief or time-limited pulsatile operation is produced.

A simple regulation process envisages that the pump output is increased on detection of gas entry. However this can result in the pump output being increased again and again in rapid succession if there are many small gas bubbles. As an advantageous variant of embodiment it is therefore proposed that the pump output is increased after the detection of a predetermined gas quantity. This predetermined gas quantity can be a gas quantity supplied by just one gas bubble or gas quantity accumulated over a longer measuring process.

In particular, if detection is carried out in a inlet line at a distance from the blood pump, it is advantageous if the pump output is increased after a period of time that corresponds with the time that the medium requires to travel from the detector to the rotor of the pump. Acceleration of the rotor is therefore envisaged at the moment the gas bubble reaches the rotor area.

In order to allow accumulation of gas in the pump and to reduce the frequency of pulsatile operation of the blood pump, it is proposed that the pump output is only increased on expiry of a predetermined period of time following the first detected gas entry. This period of time can, for example, be greater than 3 seconds and be in the region of 5 to 30 seconds.

To expel a gas bubble from the pump a one-off increase or preferably a one-off reduction with a subsequent increase in the volumetric flow can suffice. However, it is advantageous if this procedure is carried out several times in succession. This is known as pulsed pump output. It is therefore advantageous if the pump output is pulsed over a period of more than 3 seconds, preferably more than 5 seconds.

If in a pump the pulsed pump output is varied this is known as pulsatile operation. Particularly during the filling of the pump with a fluid medium there is an increased danger of gas entering. It is therefore proposed that the pump be operated in a pulsatile manner during priming.

There are various methods of detecting the gas within the pump or an inlet line. Suitable for detecting a gas or air inclusion are, for example capacitive sensors, resistance sensors, thermoelements, multimeters, ultrasound sensors or magnetoinductive sensors. Particularly suitable are sensors that measure without contact. The detector should detect at least 0.2 ml and preferably at least 0.1 ml, for example 0.5 ml, in order to be particularly well-suited for use in connection with a blood pump.

An indirect method of detecting the gas is provided in that the power uptake of the pump is measured in relation to its power output. If, for example, the volumetric flow of the conveyed medium decreases and the power uptake of the pump increases this is a sign that gas has accumulated within the pump. As, as a rule, the volumetric flow should be kept constant, if an increase in the power uptake of the pump is detected this is sufficient to conclude that gas has accumulated within the pump.

Alternatively or additionally it is proposed that the gas is detected in that the temperature is measured at the rotor bearing. An increase in the temperature at the rotor bearing also indicates an accumulation of gas.

In design terms the task on which the invention is based is solved with a centrifugal pump with a rotor, a housing and an actuator which has a gas detector which acts on the actuator when gas is detected.

This detector can be arranged in the inlet line of the pump or in the housing of the pump. Alternatively or additionally it is envisaged that the detector is arranged on the rotor or on the rotor bearing.

An advantageous embodiment of the detector envisages that the detector is a capacitive sensor. Such sensor can measure gas in a fluid medium without coming into contact with the medium.

It is advantageous if the sensor and blood pump are connected in such a way that in the event of a defective sensor the pump runs in normal operation so that that if the sensor is defective the pump is not operated in pulsatile operation. This is achieved in that the sensor does not emit a signal when conveying the medium and emits a signal in the event of air entry.

Various embodiments of blood pumps according to the invention are shown in the drawing and will be described in further detail below.

FIG. 1 schematically shows a pump head with a controller,

FIG. 2 schematically shows a view from above of the pump head shown in FIG. 1 and FIG. 3 schematically shows cross-section through the pump head shown in FIG. 1.

The pump 1 shown in FIG. 1 is a diagonal pump as the conveyed medium emerges from the rotor obliquely to the pump shaft. Depending on the design of the pump the conveying angle of the rotor can be varied so that the pump can be designed in the complete spectrum from radial to axial in order to be adapted to the application in question. However, the pump 1 has a predominantly radial conveying part for conveying blood entering centrally at the inlet 2 by means of the rotor 3 to the outlet 4.

The blood 5 flows through the housing 6 while an actuator 7 act contactlessly on magnets 8, 9 of the rotor 3 in order to move the rotor 3. The rotor 3 is borne with a ball 10 or a pin 11. Arranged in the pin 11 is a metal cone 12 which dissipates the heat from the ball 10 to the base surface 13 of the housing.

The blood inlet 2 forms the supply line 14 which in the present case is also designed as a hose 15. Provided as the detector on this hose 15 is a capacitive switching sensor. This capacitive switching sensor 16 is connected via a line 17 to a pump control 18 which in turn is connected via a line 19 to the actuator 7 of the rotor 3. The control 18 also comprises a further line 20 to report the values of the controller to a higher-ranking device (not shown) and to receive regulation and control parameters therefrom. This controller is provided in a pump console for example.

An optional further capacitive switching sensor 21 measures, as the detector, air entry at the pump housing in order to report this via line 22 to the controller 18.

Acting as a third optional detector is a temperature measuring device 23 on the base surface 13 of the housing 6 which measures the temperature on the bearing 10, 11 by detecting the temperature on the metal cone 12. This value can also be passed on to the controller 18 via a line 24.

If a gas bubble 25 enters the housing 6 of the blood pump 1 along with the medium, which in the present case is blood 5, this gas bubble 25 can already be detected by the detector 16 while it is travelling though the hose 15. Another opportunity of discovering this gas bubble 15 is provided by the further capacitive switching sensor 21. If gas bubbles accumulate centrally in the area of the axis of the bearing of the rotor 3 the pump output decreases which can be detected by the controller 18. In addition, the temperature at the bearing changes which is determined with the temperature measuring device.

In the present case air can accumulate between the pin 11 and the inner area of the rotor 3 which can be determined by means of a capacitive sensor. An air bubble trapped there can be become trapped in such a way that is can no longer be conveyed to the outlet 4.

If a pulsatile mode or blood flow is now switched on by means of the controller 18 on the actuator 7, in the brief moment of reduced flow the air has the possibility of becoming detached from the rotor. The subsequent thrust then conveys the air bubble out of the pump through the blood outlet 4. In this way the blood pump is again cleared of air. Advantageous is a reduction over 0.1 to 2 seconds and then an increase over 0.1 to 2 second for total pulsatile operation duration of approximately 5 to 30 seconds.

In practice in the line (not shown) leading from the outlet 4 to the patient there is already a flow sensor with an integrated bubble detector, for example a clamp-on transducer IPX4. In order not to endanger the patient this sensor should continue to be positioned towards the patient. A second sensor can then be positioned directly in front of the pump 1. If this detects an air bubble the system can generate a firmly set pulsatility to convey air at the rotor out of the housing. As a rule the blood with the air is then forwarded to an oxygenator where the air can finally escape. In the example of embodiment the pulsatility for expelling the air is set to 10 seconds.

As an alternative to a clamp-on sensor provided in the inlet line a capacitive sensor 16 can be positioned on the surface of the pump housing. Such capacitive switches detect the change in the dielectric constant and convert this change into a switching signal. If, for example, there is air in the area of the rotor for more than 5 seconds a pulsatile operation of the pump 1 can be carried out for example. The switching function should be such that sensor is active in the event of air and off in normal operation (switching function "Opener" YES). This counteracts the risk of the sensor pulsating continuously in the event of a defect.

The invention claimed is:

1. Method of conveying blood or priming fluid as medium with a blood the method comprising:
   (a) detecting, via a detector, gas in the medium in an inlet line to the pump,
   (b) reducing via a controller a pump output of the pump for a period of from 0.1 to 2 seconds,
   (c) after the reducing, increasing via the controller the pump output of the pump for a period of from 0.1 to 2 seconds when the gas is detected in the medium, and
   (d) repeating steps (b) and (c) in succession as a pulsed pump output if the gas is further detected.

2. Method according to claim 1, wherein the pump is a centrifugal pump or a diagonal pump.

3. Method according to claim 1, further comprising measuring a temperature on a bearing of a rotor of the pump,
   wherein the gas is detected in that an increase in the temperature on the bearing indicates an accumulation of the gas in the pump.

4. Method according to claim 1, wherein the pump output is increased by up to 100% within the period of from 0.1 to 2 seconds.

5. Method according to claim 1, wherein before the increase the pump output is reduced by up to 100% within the period of from 0.1 to 2 seconds.

6. Method according to claim 1, wherein the pump output is increased on detection of gas entry.

7. Method according to claim 1, wherein the pump output is increased after a detection of a predetermined gas quantity.

8. Method according to claim 1, further comprising a step of determining a travel time, the travel time being a period of time required by the medium to travel from the detector to a rotor of the pump,
   wherein the pump output is increased after the travel time is finished.

9. Method according to claim 1, wherein the pump output is increased on expiry of a predetermined period of time following a first gas entry (e.g. period or time greater than 3 seconds).

10. Method according to claim 1, wherein the pump output is pulsed over a period of more than 5 seconds.

11. Method according to claim 1, wherein the pump is operated in a pulsatile manner during priming.

12. Method according to claim 1, wherein the detecting comprises:
    determining a power uptake of the pump,
    determining a power output of the pump, and
    comparing the power uptake of the pump to the power output of the pump.

13. A Blood pump, in particular centrifugal pump or diagonal pump, with a rotor, a housing and an actuator wherein the blood pump comprises a gas detector which acts on the actuator when gas is detected, wherein the gas detector is configured to detect gas in a medium in an inlet line to the blood pump, wherein the blood pump further comprises a controller configured to reduce a pump output of the blood pump for a period of from 0.1 to 2 seconds and after reducing the pump output to increase the pump output for a period of from 0.1 to 2 seconds when the gas is detected in the medium, and wherein a reduction of the pump output and an increase in the pump output are repeated in succession as a pulsed pump output if the gas is further detected.

14. Blood pump according to claim 13, wherein the detector is arranged in an inlet line to the pump.

15. Blood pump according to claim 13, wherein the detector is arranged in or on the housing.

16. Blood pump according to claim 13, wherein the detector is arranged on the rotor or on a rotor bearing.

17. Blood pump according to claim 13, wherein the detector is a contactlessly measuring sensor.

18. Blood pump according to claim 13, wherein a sensor of the detector does not send a signal during conveying of a medium and sends a signal in an event of air entry.

* * * * *

UNITED STATES PATENT AND TRADEMARK OFFICE
CERTIFICATE OF CORRECTION

PATENT NO. : 10,661,000 B2
APPLICATION NO. : 15/567716
DATED : May 26, 2020
INVENTOR(S) : Wagner et al.

Page 1 of 1

It is certified that error appears in the above-identified patent and that said Letters Patent is hereby corrected as shown below:

In the Claims

Column 5, Line 26 Claim 1 after "blood" please insert --pump,--.
Column 6, Line 24 Claim 13 change "Blood" to --blood--.
Column 6, Line 38 Claim 14 change "an" to --the--.
Column 6, Line 46 Claim 18 change "a" (second occurrence) to --the--.

Signed and Sealed this
Fourteenth Day of July, 2020

Andrei Iancu
*Director of the United States Patent and Trademark Office*